(12) United States Patent
Tsuzumitani et al.

(10) Patent No.: US 7,202,095 B2
(45) Date of Patent: Apr. 10, 2007

(54) METHOD FOR MEASURING SILICIDE PROPORTION, METHOD FOR MEASURING ANNEALING TEMPERATURE, METHOD FOR FABRICATING SEMICONDUCTOR DEVICE AND X-RAY PHOTO RECEIVER

(75) Inventors: Akihiko Tsuzumitani, Niigata (JP); Yasutoshi Okuno, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 386 days.

(21) Appl. No.: 10/751,893

(22) Filed: Jan. 7, 2004

(65) Prior Publication Data
US 2004/0137650 A1 Jul. 15, 2004

(30) Foreign Application Priority Data
Jan. 8, 2003 (JP) ............................. 2003-002383

(51) Int. Cl.
*H01L 21/66* (2006.01)
(52) U.S. Cl. .................. 438/14; 438/649; 438/651; 438/682; 438/795; 257/E21.03; 257/E27.14; 257/E27.146
(58) Field of Classification Search ................. 438/14, 438/17, 649, 651, 655, 682, 795
See application file for complete search history.

(56) References Cited

U.S. PATENT DOCUMENTS 6,173,037 B1 * 1/2001 Brouwer ..................... 378/45

6,610,181 B1 * 8/2003 Besser et al. .......... 204/192.13

FOREIGN PATENT DOCUMENTS

| JP | 05-209847 | 8/1993 |
|---|---|---|
| JP | 11-145231 | 5/1999 |

OTHER PUBLICATIONS

N type semiconductor and P type semiconductor from www.answers.com search word: MOSFET.*
Y. Hu et al., "Spectroscopic ellipsometry investigation of silicide formation by rapid thermal process", J. Vac. Sci. Technol. B., 17(5), Sep./Oct. 1999, pp. 2284-2289.

* cited by examiner

*Primary Examiner*—Hsien-Ming Lee
*Assistant Examiner*—Su C. Kim
(74) *Attorney, Agent, or Firm*—McDermott Will & Emery LLP

(57) ABSTRACT

A measurement substrate 100 in which a silicon oxide film 102, a polysilicon layer 103 and a titanium silicide layer 104 are formed over a silicon substrate 101 in this order is prepared. The measurement substrate 100 is irradiated with X-rays so that the proportions of three types of silicides with different compositions in the titanium silicide layer 104 are measured based on the intensity of hard X-rays emitted from oxygen in the silicon oxide film 102 and the intensity of hard X-rays emitted from titanium in the titanium silicide layer 104.

8 Claims, 5 Drawing Sheets

FIG. 10E

METHOD FOR MEASURING SILICIDE PROPORTION, METHOD FOR MEASURING ANNEALING TEMPERATURE, METHOD FOR FABRICATING SEMICONDUCTOR DEVICE AND X-RAY PHOTO RECEIVER

BACKGROUND OF THE INVENTION

The present invention relates to methods for measuring proportions of suicides, methods for measuring annealing temperatures, methods for fabricating semiconductor devices and x-ray photo receivers.

With recent downsizing of semiconductor devices, patterns of LSIs (Large Scale Integration devices) have become finer and finer. Techniques for operating such Large Scale Integration devices with fine patterns at high speed have also been needed. A delay time in an Large Integration devices is mainly determined by the product of a resistance and a capacitance. That is, the smaller the resistance or the capacitance is, the faster the Large Scale Integration device operates. Accordingly, techniques for reducing the resistance of gate electrodes and reducing the resistance of source and drain regions are necessary for increasing the speed of Large Scale Integration devices.

To reduce the resistance, suicides (compounds of silicon with metal, e.g., tungsten silicide) having lower resistances than conventional polysilicon electrodes are used for gate electrodes and source and drain regions. In addition, silicides using titanium, cobalt and nickel as their metal components and utilizing self-alignment, called a SALICIDE process (self-align silicide), have been intensively studied. In particular, the SALICIDE process using titanium or cobalt has been already used in mass production to reduce the resistances of gate electrodes and source and drain regions.

The silicides are formed through reaction between silicon and metal. However, even one metal element can be used to produce a plurality of types of silicides having different combining ratios of silicon and metal. Silicide reactions using cobalt, platinum, titanium and nickel are expressed as follows:

where X denotes the metals. These reactions mainly produce three types of silicides. The first two reactions occur in a region at a relatively low temperature. With respect to silicides using cobalt and titanium, the specific resistances of two silicides produced by these reactions are larger than the specific resistance of the third silicide produced by the last reaction. Accordingly, the third reaction is finally caused to form a low-resistance silicide. On the other hand, with respect to silicides of nickel, silicides produced by the first two reactions have substantially the same specific resistance, which is smaller than the specific resistance of the third silicide produced by the last reaction. Accordingly, reaction is terminated after the first two reactions. With respect to platinum, reaction terminates after the first two reactions.

A process of forming a cobalt silicide in the surface of gate, source and drain in a fabrication process of a MOS transistor will be described as an example of formation of such silicides.

Figure 10A:
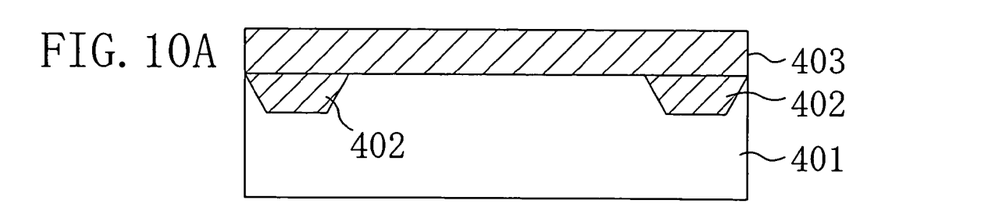
FIGS. 10A through 10E are cross-sectional views schematically showing respective process steps of forming a cobalt silicide in a MOS transistor.

First, as shown in FIG. 10A, a gate oxide film (not shown) with a thickness of about 3 nm is formed by thermal oxidation in the surface of part of a silicon substrate 401 separated by a shallow trench isolation 402. Subsequently, a polysilicon layer 403 is deposited by a CVD process to a thickness of about 150 nm thereon.

Figure 10B:
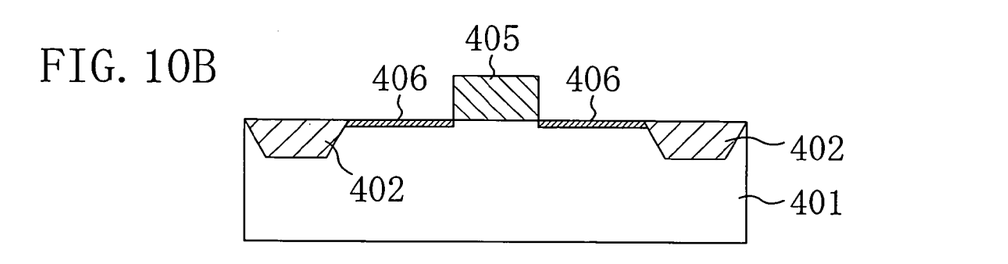

Next, as shown in FIG. 10B, ions of at least one of boron, indium, phosphorus, arsenic and antimony are implanted into the polysilicon layer 403 as an impurity, thereby defining a doped layer. Then, the doped layer is patterned to form a gate electrode 405. Thereafter, a region between the gate electrode 405 and the shallow trench isolation 402 is doped with ions as an impurity, thereby forming an LDD layer 406 as a shallow doped layer.

Figure 10C:
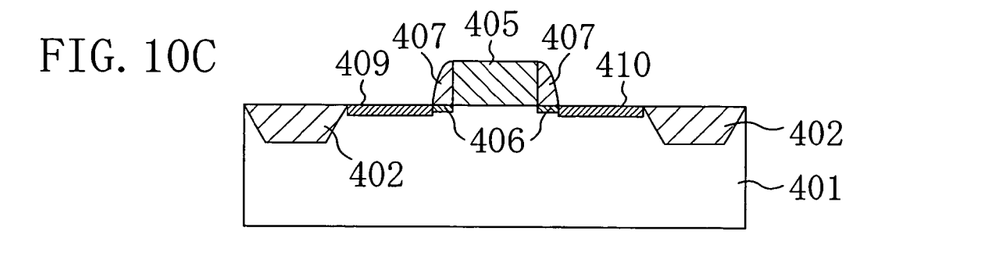

Then, a silicon oxide film is deposited by a CVD process to a thickness of about 100 nm, and anisotropic etching is performed on the silicon oxide film to expose the gate electrode 405 so that part of the silicon oxide film remains as a sidewall 407 as shown in FIG. 10C. Then, a region between the sidewall 407 and the shallow trench isolation 402 is doped with ions as an impurity, thereby forming a deeply-doped layer. Then, the deeply-doped layer is subjected to heat treatment to be activated. In this manner, source and drain layers 409 and 410 with an LDD structure are formed in an upper part of the silicon substrate 401 adjacent to the gate electrode 405.

Figure 10D:
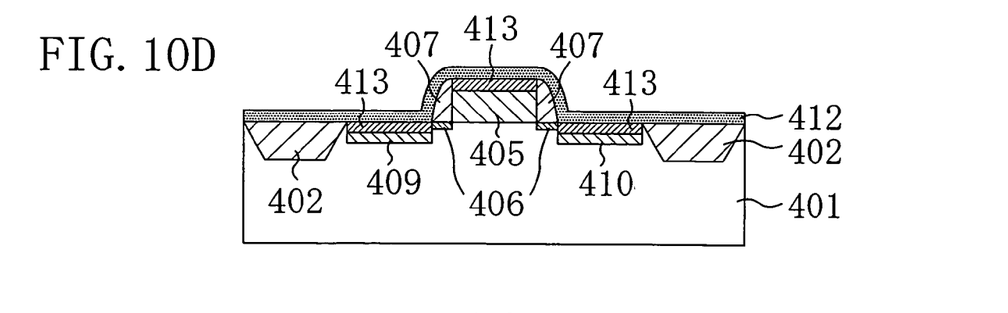

Thereafter, a silicon oxide film (natural oxide film, not shown) on the surfaces of the gate electrode 405, the source layer 409 and the drain layer 410 is removed with buffered hydrofluoric acid, and then a cobalt film with a thickness of about 10 nm is formed thereon. Then, a titanium nitride film 412 with a thickness of about 20 nm for preventing oxidation of cobalt is formed thereon as shown in FIG. 10D. Thereafter, a first rapid thermal annealing (RTA) is performed at 550° C. for 30 seconds to cause a reaction between cobalt and silicon, thereby forming a cobalt silicide layer 413. The cobalt silicide formed at this time mainly includes $Co_2Si$ and CoSi.

Figure 10E:
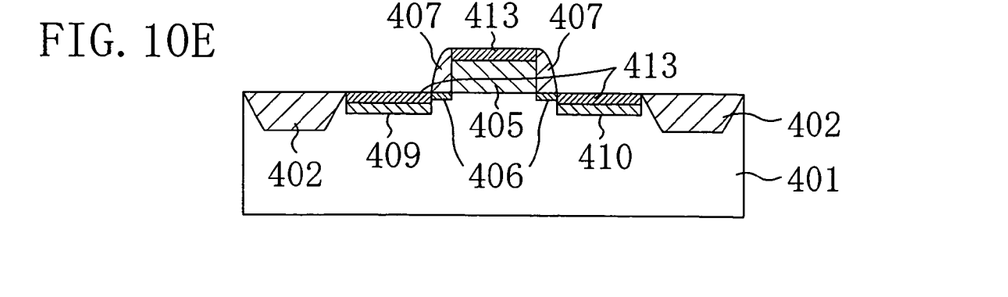

Subsequently, as shown in FIG. 10E, unreacted cobalt and the titanium nitride film 412 are removed. Then, a second RTA is performed at 850° C. for 30 seconds, thereby further reducing the resistance of the cobalt silicide layer 413 formed on the surfaces of the gate electrode 405, the source layer 409 and the drain layer 410 to obtain a silicide having a desired composition as a final product. That is, the reaction proceeds to make most of the cobalt silicide into $CoSi_2$.

In the foregoing example, the formation of the cobalt silicide layer 413 has been described. However, if titanium is used, suicides are formed with substantially the same procedure though annealing temperature regions for the RTAs are different.

In the case of formation of nickel suicides, the specific resistances of $Ni_2Si$ and NiSi do not differ extremely and $NiSi_2$ formed by annealing at 600° C. or more has a large specific resistance. Therefore, RTA is normally performed at a temperature in the range from about 400° C. to about 500° C. in the formation of nickel suicides.

Examples of measurement techniques regarding silicide include a technique described in Journal of Vacuum Society, Technology B, vol. 17, p2284 (1999), which will be detailed later.

With the foregoing processes, silicides using various types of metals are formed. With the reduction of pattern width of LSIs, tungsten as a metal element for silicides has been conventionally replaced with titanium and cobalt in order to further reduce the resistance. However, when the pattern width is reduced to 0.1 µm or less, there arise a problem of a break due to migration or the like in silicides and a problem of failure in obtaining a desired low resistance. To cope with these problems, using various metal elements and adding another material have been studied, but have not been put into actual use yet.

As another solution of the problems, a method of adjusting conditions for the first and second RTAs to make a silicide as a final product in an optimum state with low resistance and high migration resistance can be used. To obtain the silicide in this optimum state, it is necessary to know the proportions of a plurality of types of silicides having different compositions after the first RTA and it is also necessary to set conditions for the second RTA in accordance with the proportions of the silicides. In addition, it is extremely difficult to set the conditions for the second RTA if the proportions of the suicides having different compositions after the first RTA are not within an appropriated range. Accordingly, it is also necessary to control conditions for the first RTA such that these proportions are within the appropriate range. Among the conditions for the first RTA, it is important to strictly control the annealing temperature, i.e., the temperature which a silicon substrate reaches in the first RTA. This is because no silicide with a desired resistance is obtained finally unless this temperature is controlled within the variation of ±5° C.

In other words, the measurement of the three proportions of $X_2Si$, $XSi$ and $XSi_2$, respectively, after the first RTA, and the control of the temperature in the first RTA, are important. With respect to the former, the proportions have been estimated using sheet resistance measurement to date. As a new method, measurement using a spectroscopic ellipsometry which is an optical technique has been studied (e.g., in Journal of Vacuum Society, Technology B, vol. 17, p2284 (1999)). On the other hand, with respect to the latter, temperature measurements by measuring a change in thickness of a silicon oxide film or a change in the sheet resistance after ion implantation, direct temperature measurement with a thermocouple, and other methods have been studied.

With the sheet resistance measurement as the former measurement technique, the proportions of the respective silicides are estimated using the fact that $X_2Si$, $XSi$ and $XSi_2$ have respective specific resistances. The total amount of metal can also be measured by measuring a peak intensity of fluorescence X-rays from metal such as cobalt with an x-ray fluorescence measurement.

With the measurement of a change in silicon oxide film thickness as the latter measurement technique, the annealing temperature is measured, using the fact that the silicon oxide film has its thickness increased when annealed in an oxidation ambient. With the measurement of a change in the sheet resistance after ion implantation, annealing on the silicon substrate doped with ions activates the ions so that the sheet resistance changes. It is possible to know the annealing temperature utilizing this phenomenon.

However, in the case of measuring the sheet resistance, the proportions cannot be measured directly and the specific resistance also changes depending on the crystallinity of suicides and the like, so that it is extremely difficult to calculate the proportions of the silicides with high accuracy. In addition, since the sheet resistance is measured by a 4-point probe method, the measurement is easily performed on a silicon substrate or the like, but is not easily performed on a device with a complicated pattern in performing in-line measurement in fabrication process steps. The spectroscopic ellipsometry allows measurement of the proportions of the silicides theoretically, but has not been put into practical use yet.

Since the first RTA is performed at a relatively low temperature of about 500° C., the thickness of the silicon oxide film and the sheet resistance after ion implantation vary slightly even after the first RTA. Accordingly, it is very difficult to accurately measure the temperature in the first RTA using the change in thickness of the silicon oxide film or the change in sheet resistance. In addition, since the thermocouple measures the temperature of a specific part of annealing apparatus, the temperature of the silicon substrate cannot be measured accurately. The annealing temperature may be measured with a thermocouple attached to the silicon substrate at the first use of new annealing apparatus. However, this technique is not suitable for mass production. Therefore, no techniques have been found to date in accurately measuring the annealing temperature in the first RTA in fabrication.

SUMMARY OF THE INVENTION

It is therefore an object of the present invention to provide a method for easily measuring the proportions of a plurality of types of silicides having different compositions with high accuracy. It is another object of the present invention to provide a method for easily measuring the annealing temperature in the first RTA, a method for fabricating a semiconductor device using these measuring methods and an x-ray photo receiver suitable for these methods.

A first inventive method for measuring silicide proportions includes the steps of: preparing a measurement substrate including: a substrate including a silicon layer at least at the surface thereof; a silicon oxide film or a silicon nitride film formed on the silicon layer; a polysilicon layer or an amorphous silicon layer formed over the silicon oxide film or the silicon nitride film; and a silicide layer formed in the surface of the polysilicon layer or the amorphous silicon layer and made of a plurality of types of silicides having different combining ratios of metal and silicon; irradiating the measurement substrate with X-rays; measuring the intensity of hard X-rays emitted from oxygen in the silicon oxide film or nitrogen in the silicon nitride film by the irradiation with the X-rays, and the intensity of hard X-rays emitted from the metal in the silicide layer by the irradiation with the X-rays; and calculating proportions of the plurality of types of silicides in the silicide layer, from the intensities of the two types of the hard X-rays.

A second inventive method for measuring silicide proportions includes the steps of: preparing a measurement substrate including: a substrate including a silicon layer at least at the surface thereof; a doped layer formed by implanting a dopant into the surface of the silicon layer; and a silicide layer formed in the surface of the doped layer and made of a plurality of types of silicides having different combining ratios of metal and silicon; irradiating the measurement substrate with X-rays; measuring the intensity of hard X-rays or ultra-soft X-rays emitted from the dopant in the doped layer by the irradiation with the X-rays, and the intensity of hard X-rays emitted from the metal in the silicide layer by the irradiation with the X-rays; and calculating proportions of the plurality of types of silicides in the silicide layer, from either the intensities of the two types of the hard X-rays or the intensities of the ultra-soft X-rays and the hard X-rays emitted from the metal.

A third inventive method for measuring silicide proportions includes the steps of: preparing a measurement substrate including: a substrate including a silicon layer at least at the surface thereof; a silicon oxide film or a silicon nitride film formed on the silicon layer; a doped layer formed by implanting a dopant into a polysilicon layer or an amorphous silicon layer formed over the silicon oxide film or the silicon nitride film; and a silicide layer formed in the surface of the doped layer and made of a plurality of types of silicides having different combining ratios of metal and silicon; irradiating the measurement substrate with X-rays; measuring the intensity of hard X-rays emitted from oxygen in the silicon oxide film or nitrogen in the silicon nitride film by the irradiation with the X-rays, the intensity of hard X-rays or ultra-soft X-rays emitted from the dopant in the doped layer by the irradiation with the X-rays, and the intensity of hard X-rays emitted from the metal in the silicide layer by the irradiation with the X-rays; and calculating proportions of the plurality of types of silicides in the silicide layer, from either the intensities of the three types of the hard X-rays or the intensities of the hard X-rays emitted from the oxygen or the nitrogen, the ultra-soft X-rays and the hard X-rays emitted from the metal.

A first inventive method for measuring an annealing temperature includes the steps of: preparing a measurement substrate including: a substrate including a silicon layer at least at the surface thereof; a silicon oxide film or a silicon nitride film formed on the silicon layer; a polysilicon layer or an amorphous silicon layer formed over the silicon oxide film or the silicon nitride film; and a metal layer formed over the polysilicon layer or the amorphous silicon layer; annealing the measurement substrate at a given temperature, thereby changing at least part of the polysilicon layer or the amorphous silicon layer and at least part of the metal layer into a silicide layer made of a plurality of types of suicides having different combining ratios of metal and silicon; irradiating the measurement substrate with X-rays after the step of forming the silicide layer has been performed; measuring the intensity of hard X-rays emitted from oxygen in the silicon oxide film or nitrogen in the silicon nitride film by the irradiation with the X-rays, and the intensity of hard X-rays emitted from the metal in the silicide layer by the irradiation with the X-rays; and calculating the given temperature from the intensities of the two types of the hard X-rays.

A second inventive method for measuring an annealing temperature includes the steps of: preparing a measurement substrate including: a substrate including a silicon layer at least at the surface thereof; a doped layer formed by implanting a dopant into the surface of the silicon layer; and a metal layer formed over the doped layer; annealing the measurement substrate at a given temperature, thereby changing at least part of the doped layer and at least part of the metal layer into a silicide layer made of a plurality of types of suicides having different combining ratios of metal and silicon; irradiating the measurement substrate with X-rays after the step of forming the silicide layer has been performed; measuring the intensity of hard X-rays or ultra-soft X-rays emitted from the dopant in the doped layer by the irradiation with the X-rays, and the intensity of hard X-rays emitted from the metal in the silicide layer by the irradiation with the X-rays; and calculating the given temperature from either the intensities of the two types of the hard X-rays or the intensities of the ultra-soft X-rays and the hard X-rays emitted from the metal.

A third inventive method for measuring an annealing temperature includes the steps of: preparing a measurement substrate including: a substrate including a silicon layer at least at the surface thereof; a silicon oxide film or a silicon nitride film formed on the silicon layer; a doped layer formed by implanting a dopant into a polysilicon layer or an amorphous silicon layer formed over the silicon oxide film or the silicon nitride film; and a metal layer formed over the surface of the doped layer; annealing the measurement substrate at a given temperature, thereby changing at least part of the doped layer and at least part of the metal layer into a silicide layer made of a plurality of types of silicides having different combining ratios of metal and silicon; irradiating the measurement substrate with X-rays after the step of forming the silicide layer has been performed; measuring the intensity of hard X-rays emitted from oxygen in the silicon oxide film or nitrogen in the silicon nitride film by the irradiation with the X-rays, the intensity of hard X-rays or ultra-soft X-rays emitted from the dopant in the doped layer by the irradiation with the X-rays, and the intensity of hard X-rays emitted from the metal in the silicide layer by the irradiation with the X-rays; and calculating the given temperature from either the intensities of the three types of the hard X-rays or the intensities of the hard X-rays emitted from the oxygen or the nitrogen, the ultra-soft X-rays and the hard X-rays emitted from the metal.

A first inventive method for fabricating a semiconductor device includes the steps of: forming a silicon oxide film or a silicon nitride film on a silicon layer included in a substrate which includes the silicon layer at least at the surface thereof; forming a polysilicon layer or an amorphous silicon layer over the silicon oxide film or the silicon nitride film; forming a metal layer over the polysilicon layer or the amorphous silicon layer; annealing the polysilicon layer or the amorphous silicon layer and the metal layer at a first temperature, thereby forming a silicide layer made of a plurality of types of silicides having different combining ratios of metal and silicon; irradiating the substrate with X-rays after the step of forming the silicide layer has been performed; measuring the intensity of hard X-rays emitted from oxygen in the silicon oxide film or nitrogen in the silicon nitride film by the irradiation with the X-rays and the intensity of hard X-rays emitted from the metal in the silicide layer by the irradiation with the X-rays, and calculating proportions of the plurality of types of silicides in the silicide layer, from the intensities of the two types of the hard X-rays; and annealing the silicide layer at a second temperature which is calculated from the proportions of the plurality of types of suicides.

A second inventive method for fabricating a semiconductor device includes the steps of: implanting a dopant into the surface of a silicon layer included in a substrate which includes the silicon layer at least at the surface thereof, thereby forming a doped layer; forming a metal layer over the doped layer; annealing the doped layer and the metal layer at a first temperature, thereby forming a silicide layer made of a plurality of types of suicides having different combining ratios of metal and silicon; irradiating the substrate with X-rays after the step of forming the silicide layer has been performed; measuring the intensity of hard X-rays or ultra-soft X-rays emitted from the dopant in the doped layer by the irradiation with the X-rays and the intensity of hard X-rays emitted from the metal in the silicide layer by the irradiation with the X-rays, and calculating proportions of the plurality of types of silicides in the silicide layer, from either the intensities of the two types of the hard X-rays or the intensities of the ultra-soft X-rays and the hard X-rays emitted from the metal; and annealing the silicide layer at a second temperature which is calculated from the proportions of the plurality of types of silicides.

A third inventive method for fabricating a semiconductor device includes the steps of: forming a silicon oxide film or a silicon nitride film on a silicon layer included in a substrate which includes the silicon layer at least at the surface thereof; forming a polysilicon layer or an amorphous silicon layer over the silicon oxide film or the silicon nitride film;

implanting a dopant into the polysilicon layer or the amorphous silicon layer, thereby forming a doped layer; forming a metal layer over the doped layer; annealing the doped layer and the metal layer at a first temperature, thereby forming a silicide layer made of a plurality of types of suicides having different combining ratios of metal and silicon; irradiating the substrate with X-rays after the step of forming the silicide layer has been performed; measuring the intensity of hard X-rays emitted from oxygen in the silicon oxide film or nitrogen in the silicon nitride film by the irradiation with the X-rays, the intensity of hard X-rays or ultra-soft X-rays emitted from the dopant in the doped layer by the irradiation of the X-rays and the intensity of hard X-rays emitted from the metal in the silicide layer by the irradiation with the X-rays; calculating proportions of the plurality of types of silicides in the silicide layer, from either the intensities of the three types of the hard X-rays or the intensities of the hard X-rays emitted from the oxygen or the nitrogen, the ultra-soft X-rays and the hard X-rays from the metal; and annealing the silicide layer at a second temperature which is calculated from the proportions of the plurality of types of silicides.

A first inventive x-ray photo receiver, formed on a silicon layer included in a substrate which includes the silicon layer at least at the surface thereof and on which a semiconductor integrated circuit is formed, includes: an x-ray receiving surface for an x-ray fluorescence analysis; a silicon oxide film or a silicon nitride film formed on a region of the substrate on which no semiconductor integrated circuit is present; and a silicide layer formed over the silicon oxide film or the silicon nitride film and made of a plurality of types of silicides having different combining ratios of metal and silicon, wherein the x-ray receiving surface has an area larger than an irradiation spot for first X-rays for use in the x-ray fluorescence analysis.

A second inventive x-ray photo receiver, formed on a silicon layer included in a substrate which includes the silicon layer at least at the surface thereof and on which a semiconductor integrated circuit is formed, includes: an x-ray receiving surface for an x-ray fluorescence analysis; a doped layer formed by implanting a dopant in a region of the substrate on which no semiconductor integrated circuit is present; and a silicide layer formed in the surface of the doped layer and made of a plurality of types of suicides having different combining ratios of metal and silicon, wherein the x-ray receiving surface has an area larger than an irradiation spot for first X-rays for use in the x-ray fluorescence analysis.

A third inventive x-ray photo receiver, formed on a silicon layer included in a substrate which includes the silicon layer at least at the surface thereof and on which a semiconductor integrated circuit is formed, includes: an x-ray receiving surface for an x-ray fluorescence analysis; a silicon oxide film or a silicon nitride film formed on a region of the substrate on which no semiconductor integrated circuit is present; a doped layer formed by implanting a dopant into a polysilicon layer or an amorphous silicon layer formed over the silicon oxide film or the silicon nitride film; and a silicide layer formed in the surface of the doped layer and made of a plurality of types of silicides having different combining ratios of metal and silicon, wherein the x-ray receiving surface has an area larger than an irradiation spot for first X-rays for use in the x-ray fluorescence analysis.

The metal preferably contains a metal element having a high melting point.

The metal element preferably has a high melting point of 1400° C. or more, and is tungsten (melting point : 3382° C.), platinum (melting point: 1774° C.), titanium (melting point: 1725° C.), cobalt (melting point: 1492° C.) and nickel (melting point: 1455° C.), for example. The upper limit of metal constituting a useful silicide is 3382° C.

The metal is preferably made of at least one material selected from the group consisting of titanium, cobalt, nickel and platinum.

The dopant is preferably made of at least one material selected from the group consisting of boron, phosphorus, arsenic, germanium, antimony and indium.

DESCRIPTION OF THE PREFERRED EMBODIMENTS

Hereinafter, embodiments of the present invention will be described with reference to the drawings. A substrate herein includes substrates such as a substrate with two or more layers in which a silicon oxide film is formed on a silicon layer, for example, as well as a substrate with only one layer such as a silicon substrate, for convenience.

Embodiment 1

Figure 1:
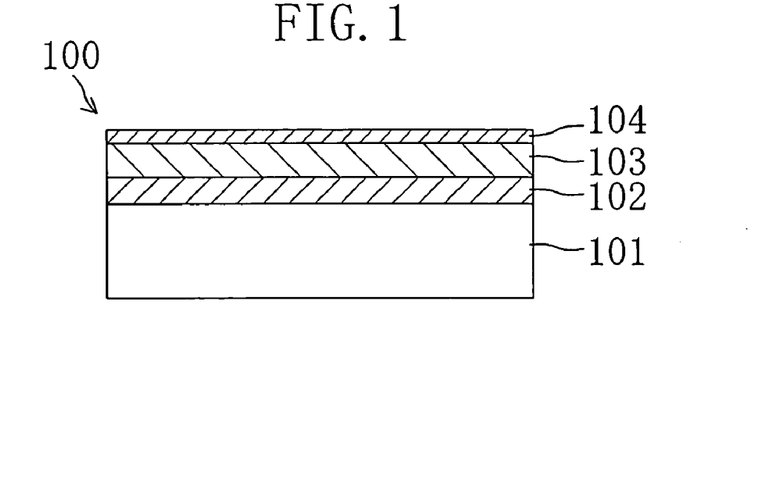
FIG. 1 is a cross-sectional view schematically showing a measurement substrate according to a first embodiment of the present invention.

As shown in FIG. 1, a substrate 100 for measurement (hereinafter, referred to as a measurement substrate) according to this embodiment includes: a silicon substrate (substrate) 101; a silicon oxide film 102; a polysilicon layer 103; and a titanium silicide layer 104. The silicon oxide film 102, the polysilicon layer 103 and the titanium silicide layer 104 are formed on the silicon substrate 101 in this order. A plurality of types of titanium silicides having different compositions included in the titanium silicide layer 104 are formed by a first RTA and have their proportions changed by a second RTA.

Figure 2:
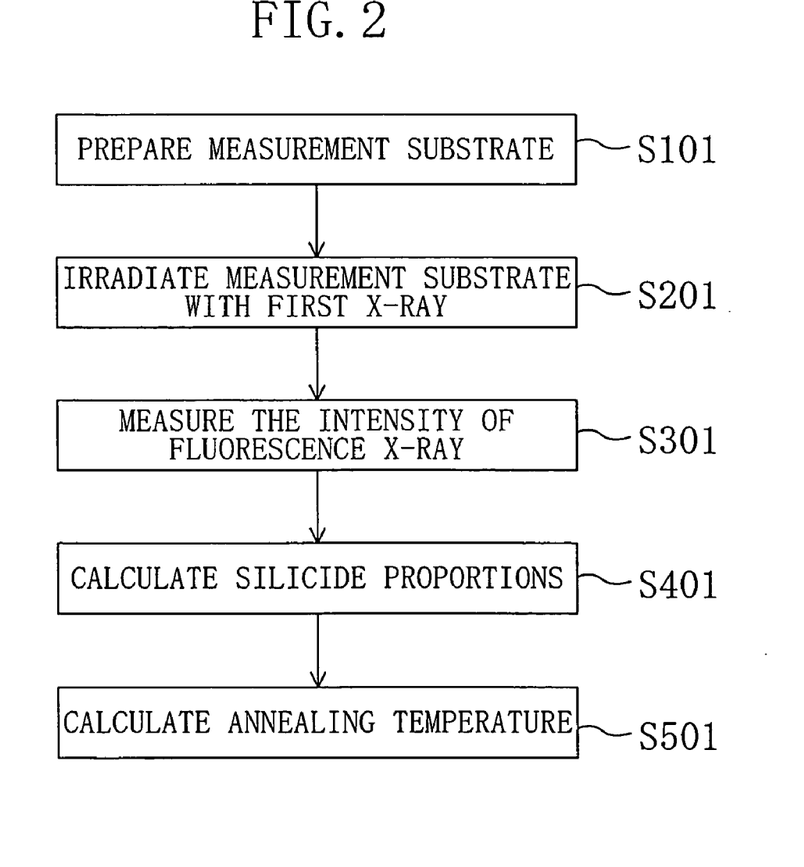
FIG. 2 is a flowchart showing a method for measuring silicide proportions and a method for measuring annealing temperatures.

In this embodiment, an x-ray fluorescence analysis is conducted to measure the proportions of the titanium silicides contained in the titanium silicide layer 104. As shown in FIG. 2, this measurement includes: step S101 of preparing the measurement substrate 100; step S201 of irradiating the measurement substrate 100 with first X-rays; step S301 of measuring the intensity of fluorescence X-rays applied; and step S401 of calculating the proportions of the silicides from the intensity of the fluorescence X-rays. A method for measuring the temperature in the first RTA includes step S501 of calculating the annealing temperature from the proportions of the silicides, in addition to the four steps S101, S201, S301 and S401.

The x-ray fluorescence analysis uses hard X-rays emitted from oxygen in the silicon oxide film 102 and hard X-rays emitted from titanium in the titanium silicide layer 104. The hard X-rays emitted from oxygen in the silicon oxide film 102 are partly absorbed in the polysilicon layer 103 and the titanium silicide layer 104 (including $Ti_2Si$, $TiSi$ and $TiSi_2$) which are located above the silicon oxide film 102.

The hard X-rays from oxygen actually observed above the titanium silicide layer 104 have an intensity $I_O$ which is equal to the value obtained by subtracting the absorbed amount $A_{poly}$ of the hard X-rays from oxygen in the polysilicon layer 103 and the absorbed amounts of $A_{Ti2Si}$, $A_{TiSi}$ and $A_{TiSi2}$ of the hard X-rays from oxygen in the respective silicides, from the intensity $I_{Oini}$ of the hard X-rays from oxygen in the absence of the polysilicon layer 103 and the titanium silicide layer 104 above the silicon oxide film 102. Accordingly, the intensity $I_O$ is expressed as follows:

$$I_O = I_{Oini} - A_{poly} - A_{Ti2Si} - A_{TiSi} - A_{TiSi2}$$

From the relationship among absorption coefficients of X-rays, the above equation is also expressed as follows:

$$I_O = I_{Oini} \exp(-\mu_{poly} \cdot t_{poly} - \mu_{Ti2Si} \cdot t_{Ti2Si} - \mu_{TiSi} \cdot t_{TiSi} - \mu_{TiSi2} \cdot t_{TiSi2})$$

where $\mu_Y$ is the absorption coefficient of the hard X-rays from oxygen in a material Y, $t_Y$ is the thickness of the material Y (i.e., the thickness of a layer of the material Y on the assumption that materials gather individually to form respective layer structures).

Figure 3:
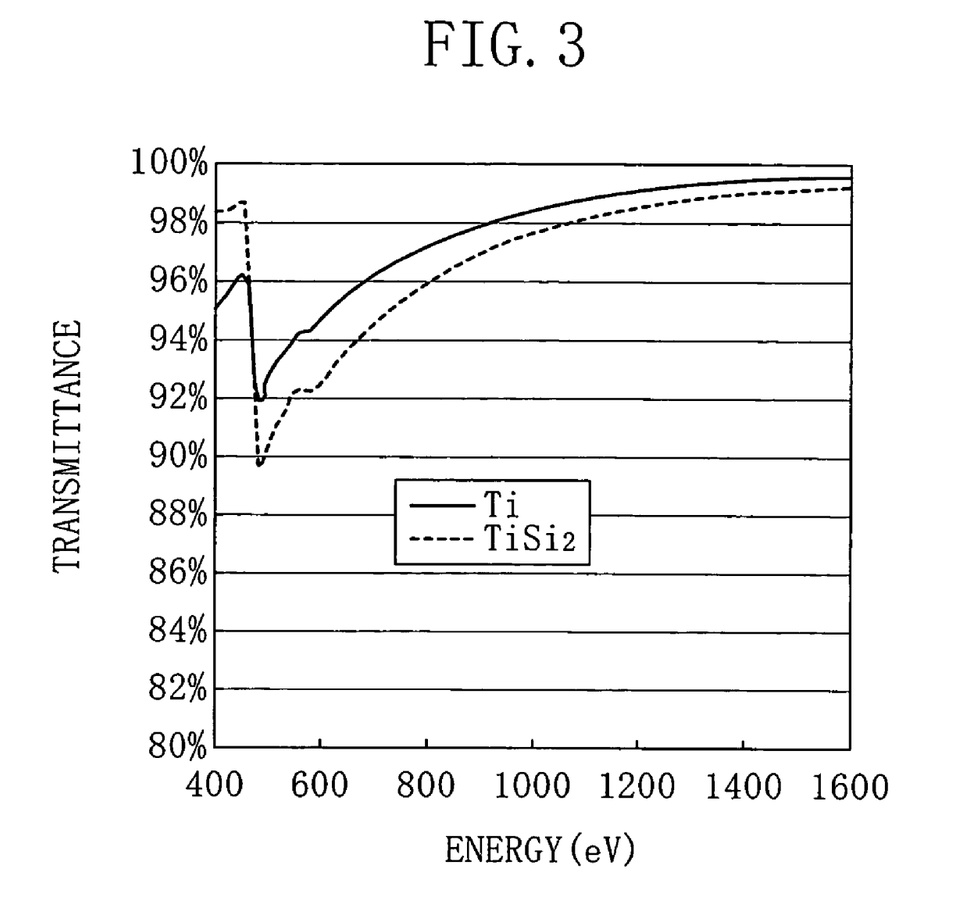
FIG. 3 is a graph showing calculation results of energy dependences of x-ray transmittance in titanium and $TiSi_2$ each with a thickness of 10 nm.

Once the absorption coefficients $\mu_Y$, $I_{Oini}$ and $t_{poly}$ in the above equation are determined, an equation between the intensity $I_O$ of the observed hard X-rays from oxygen and the thicknesses (translatable into proportions) of the silicides having respective compositions is obtained. Among these coefficients, $I_{Oini}$ and $\mu_{poly}$ are obtained by measuring a standard sample and $t_{poly}$ is obtained by measuring an optical system. From FIG. 3, the x-ray absorption coefficient ($\mu_{TiSi2}$) of a $TiSi_2$ film with a thickness of 10 nm is obtained by calculation and is 8% at 550 eV at which the hard X-rays from oxygen are observed. In the same manner, the values of the coefficients $\mu_{Ti2Si}$ and $\mu_{TiSi}$ are also obtained. The x-ray absorption coefficient can be obtained with high accuracy by forming a standard sample separately. The x-ray absorption coefficient of a titanium film with a thickness of 10 nm is 6% at 550 eV from FIG. 3. In this manner, all the absorption coefficients $\mu_Y$, $I_{Oini}$, and $t_{poly}$ are determined, so that an equation between the intensity $I_O$ of the observed hard X-rays from oxygen and the thicknesses $t_{Ti2Si}$, $t_{TiSi}$ and $t_{TiSi2}$ of the suicides with respective compositions is obtained.

From the intensity of the observed hard X-rays from titanium, an equation between this intensity and the thicknesses of the three types of titanium suicides is also obtained. Three unknown thicknesses of the suicides with respective compositions are provided to each of these two equations. Accordingly, fluorescence X-rays applied to a large number of measurement substrates 100 are measured, and a hypothetical equation expressed by the thicknesses of the three types of titanium suicides is formed based on the measured values. Then, the thicknesses of the three types of titanium suicides are calculated using the simultaneous equations thus obtained. Since the densities of the titanium suicides are known, the proportions of the three titanium silicides are calculated from these thicknesses.

Once the proportions are obtained from the calculation results, the annealing temperature in the first RTA is determined. Specifically, heat history of the first RTA performed on the measurement substrate 100 determines the proportions of the three types of titanium silicides uniquely, so that the annealing temperature is calculated backward from the proportions. Even if the annealing temperature in the first RTA slightly varies, the proportions of the three types of titanium silicides change relatively largely. Accordingly, the annealing temperature can be obtained from the calculation accurately with the method of this embodiment.

In addition, it is necessary to have the reaction proceed to finally obtain $TiSi_2$ with a relatively low resistance through the second RTA. The optimum annealing temperature in the second RTA is determined by the proportions of the three types of titanium silicides after the first RTA. Therefore, the annealing temperature in the second RTA is calculated from the proportions so that the second RTA is conducted at the obtained temperature. This calculation may be performed by, for example, using a graph of the relationship between the silicide proportions and the annealing temperature in the second RTA obtained through an experiment beforehand.

In this embodiment, both the fluorescence X-rays (hard X-rays) from oxygen and the fluorescence X-rays (hard X-rays) from titanium are measured for calculation, so that the proportions of a plurality of types of suicides having different compositions are obtained easily with high accuracy. In addition, the annealing temperature in the first RTA is calculated from these proportions with accuracy. Accordingly, it is possible to set the annealing temperature in the second RTA easily such that an optimum silicide with low resistance and high reliability is formed. Otherwise, it is also possible to set the annealing temperature in the first RTA to increase a margin for the annealing temperature in the second RTA with which the optimum silicide is formed. In this manner, the optimum silicide is formed with high yield of devices.

Now, a method for fabricating the measurement substrate 100 of this embodiment will be described.

First, a silicon oxide film 102 is formed by thermal oxidation in the surface of the silicon substrate 101. Then, a polysilicon layer 103 is formed by, for example, a CVD process thereon. Subsequently, titanium is deposited by, for example, a sputtering process over the polysilicon layer 103, thereby forming a titanium metal layer. To prevent oxidation of this titanium metal layer, titanium nitride is further deposited over the titanium metal layer, thereby forming a titanium nitride layer.

Thereafter, the measurement substrate 100 in which the film and layers described above have been formed over the silicon substrate 101 is subjected to heat treatment at a given temperature (a first temperature) of 600° C. for 30 seconds, thus performing a first RTA. The first RTA makes part of the polysilicon layer 103 react with part of the titanium metal layer, thereby forming a titanium silicide layer 104. Then, the unreacted titanium metal layer and the titanium nitride layer are removed with a chemical solution. The titanium silicide at this time is in a mixed-crystal state, i.e., is made of $Ti_2Si$, $TiSi$ and $TiSi_2$. The process up to this state will be referred to as step S101 of preparing the measurement substrate 100.

Next, the measurement substrate 100 after the first RTA, i.e., the silicon oxide film 102, the polysilicon layer 103 and the titanium silicide layer 104 over the silicon substrate 101, is irradiated with first X-rays for use in an x-ray fluorescence analysis (step S201). Subsequently, the intensity of hard X-rays emitted from a titanium element in the titanium silicide layer 104 and the intensity of hard X-rays emitted from oxygen in the silicon oxide film 102 out of the fluorescence X-rays emitted from these film and layers to a space over the titanium silicide layer 104 are measured (step S301).

Thereafter, the proportions of the three types of titanium silicides are calculated from the intensities of the two types of the hard X-rays in the manner described above (step S401), and an annealing temperature in the first RTA is calculated into the proportions (step S501).

Then, temperature (second temperature) at which a second RTA should be performed is calculated from the proportions, and the second RTA is performed at the obtained temperature so that the reaction proceeds to change substantially all the titanium silicides into $TiSi_2$ with low resistance. In this manner, the measurement substrate 100 of this embodiment is achieved.

Figure 4:
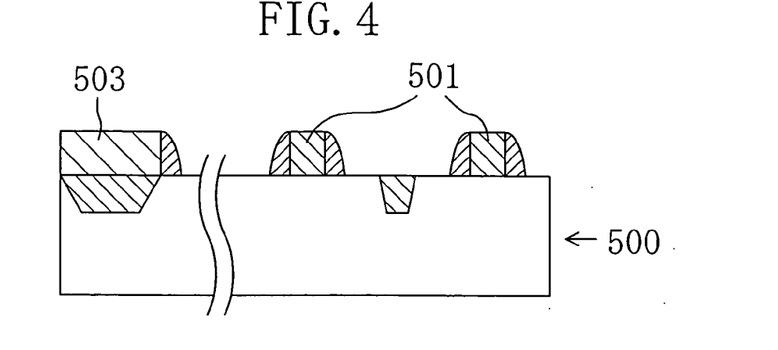
FIG. 4 is a cross-sectional view schematically showing a semiconductor device according to a modified example 1-1.

In this embodiment, polysilicon is not patterned specifically. On the other hand, in a semiconductor device 500 according to a modified example 1-1 of the this embodiment, a semiconductor integrated circuit (e.g., a gate electrode 501) is formed by patterning as shown in FIG. 4 and an x-ray photo receiver 503 is provided. In this modified example, fluorescence X-rays are measured utilizing the x-ray photo receiver 503 so that the proportions of titanium suicides and annealing temperatures are measured.

First X-rays for the x-ray fluorescence analysis are applied onto the upper surface of the x-ray photo receiver 503 as an x-ray receiving surface shown in FIG. 4. The area of the x-ray receiving surface is larger than an irradiation spot at a source of the applied X-rays for the x-ray fluorescence analysis. Accordingly, all the first X-rays are applied onto the x-ray photo receiver 503, and all the applied fluorescence X-rays are derived from materials in the x-ray photo receiver 503. Specifically, the applied fluorescence X-rays include only a signal for measuring the proportions of the titanium silicides and no noise is mixed therein. The area of the x-ray receiving surface is preferably smaller than a 1-mm-square and is more preferably smaller than 500-μm-square.

The x-ray photo receiver 503 is usually formed on, for example, an end of a silicon wafer which is finally disposed of, such as a scribe line, in a process of mass production of transistors. Accordingly, the yield of transistors does not decrease and no additional processes are needed.

The x-ray photo receiver 503 of the modified example 1-1 is fabricated on a silicon wafer with the same process as the above-described method for the substrate 100. Specifically, in the process for fabricating the semiconductor device 500, a silicon oxide film is formed in the surface of a substrate including a silicon layer at least at its surface, and a polysilicon layer, a titanium metal layer and a titanium nitride layer are formed over the silicon oxide film. Then, a first RTA (annealing) is performed. The x-ray photo receiver 503 thus fabricated is irradiated with X-rays, and the silicide proportions are measured with an x-ray fluorescence analysis. Then, a second RTA (annealing) is performed based on a result of the measurement. Each of the formation process steps and annealing process steps described above is performed concurrently with the corresponding process step for fabricating transistors on the silicon wafer.

In this modified example, a sidewall or a separation oxide film may be provided around the x-ray photo receiver 503. In a case where such an x-ray photo receiver 503 is provided on the silicon wafer, if an x-ray fluorescence analysis instrument is incorporated in fabrication apparatus beforehand, the proportions of a plurality of types of silicides formed in the semiconductor device during fabrication can be directly measured in an in-line measurement, so that process steps are managed more easily.

Now, modified examples 1-2 and 1-3 of this embodiment will be described. The modified example 1-2 is a semiconductor device in which amorphous silicon is used instead of polysilicon and an x-ray photo receiver is provided. The modified example 1-3 is a semiconductor device in which a silicon nitride film is used instead of the silicon oxide film 102 and an x-ray photo receiver is provided. Measurement of fluorescence X-rays and calculation to obtain the proportions of silicides and annealing temperatures are performed in the same manner as in the first embodiment. With respect to the fabrication process, the process step of forming a polysilicon layer is substituted by a publicly-known process step of forming an amorphous silicon layer in the modified example 1-2, and the process step of forming a silicon oxide film is substituted by a publicly-known process step of forming a silicon nitride film in the modified example of 1-3. Other process steps are the same as those described above. In the modified example 1-3, hard X-rays emitted from nitrogen are used for measurement, instead of hard X-rays emitted from oxygen.

In the modified examples of this embodiment, both the fluorescence X-rays (hard X-rays) emitted from oxygen or nitrogen and the fluorescence X-rays (hard X-rays) emitted from titanium are measured, so that the proportions of a plurality of types of silicides having different compositions are obtained easily in an in-line measurement with high accuracy. The annealing temperature in the first RTA is calculated from the proportions with high accuracy. Accordingly, it is possible to set the annealing temperature in the second RTA such that an optimum silicide with low resistance and high reliability is formed. Otherwise, it is also possible to set the annealing temperature in the first RTA to increase a margin for the annealing temperature in the second RTA with which the optimum silicide is formed. In this manner, an optimum silicide is formed with high yield of devices. If an x-ray fluorescence analysis instrument is incorporated during fabrication such that measurement and calculation are automatically performed under computer control, for example, processes are managed much easily, thus reducing fabrication costs.

Embodiment 2

Figure 5:
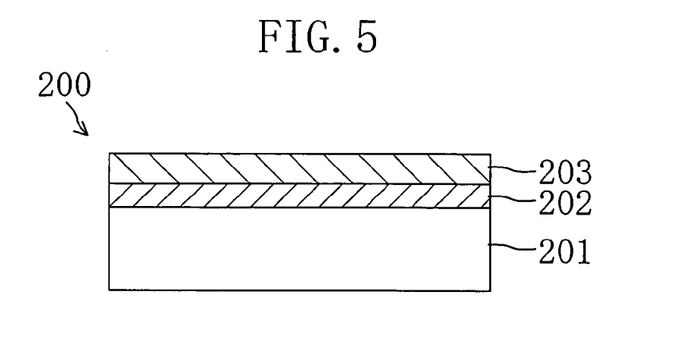
FIG. 5 is a cross-sectional view schematically showing a measurement substrate according to a second embodiment of the present invention.

As shown in FIG. 5, a measurement substrate 200 according to this embodiment includes: a silicon substrate (substrate) 201; a doped layer 202 formed by implanting arsenic; and a cobalt silicide layer 203. The doped layer 202 and the cobalt silicide layer 203 are formed over the silicon substrate 201 in this order. A plurality of types of cobalt suicides having different compositions included in the cobalt silicide layer 203 are formed by a first RTA and have their proportions changed by a second RTA.

In this embodiment, an x-ray fluorescence analysis is performed to measure the proportions of cobalt suicides in the cobalt silicide layer 203. As shown in FIG. 2, this measurement includes: step S101 of preparing the measurement substrate 100; step S201 of irradiating the measurement substrate 100 with first X-rays; step S301 of measuring the intensity of fluorescence X-rays applied; step S401 of calculating the proportions of the suicides from the intensity of the fluorescence X-rays. A method for measuring the temperature in the first RTA includes step S501 of calculating the annealing temperature from the proportions of the silicides, in addition to the four steps S101, S201, S301 and S401.

The x-ray fluorescence analysis uses hard X-rays emitted from arsenic in the doped layer 202 and hard X-rays emitted from cobalt in the cobalt silicide layer 203. The hard X-rays emitted from arsenic in the doped layer 202 are partly absorbed in the cobalt silicide layer 203 (including $Co_2Si$, $CoSi$ and $CoSi_2$) which is located above the doped layer 202.

The hard X-rays from arsenic actually observed above the cobalt silicide layer 203 have an intensity $I_{As}$ which is equal to the value obtained by subtracting the absorbed amount $A_{AsCo2Si}$, $A_{AsCoSi}$ and $A_{AsCoSi2}$ of the hard X-rays from arsenic in the respective silicides, from the intensity $I_{Asini}$ of the hard X-rays from arsenic in the absence of the cobalt silicide layer 203 above the doped layer 202. Accordingly, the intensity $I_{As}$ is expressed as follows:

$$I_{As}=I_{Asini}-A_{AsCo2Si}-A_{AsCoSi}-A_{AsCoSi2}$$

From the relationship among absorption coefficients of X-rays, the above equation is also expressed as follows:

$$I_{As}=I_{Asini}\exp(-\mu_{AsCo2Si}\cdot t_{Co2Si}-\mu_{AsCoSi}\cdot t_{CoSi}-\mu_{AsCoSi2}\cdot t_{CoSi2})$$

where $\mu_{AsY}$ is the absorption coefficient of the hard X-rays from arsenic in a material Y, $t_Y$ is the thickness of the material Y (i.e., the thickness of a layer of the material Y on the assumption that materials gather individually to form respective layer structures).

Figure 6:
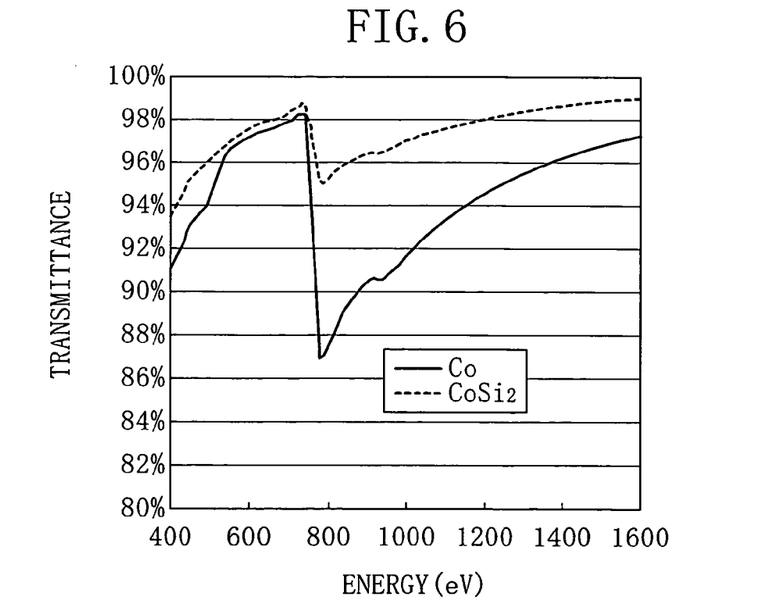
FIG. 6 is a graph showing calculation results of energy dependences of x-ray transmittance in cobalt and $CoSi_2$ each with a thickness of 10 nm.

Once the absorption coefficients $\mu_{AsY}$ and $t_{Asini}$ in the above equations are determined, the equation between the intensity $I_{As}$ of the observed hard X-rays from arsenic and the thicknesses (translatable into proportions) of the suicides with different compositions is obtained. Among these coefficients, $I_{Asini}$ is obtained by measuring a standard sample. On the other hand, from FIG. 6, the x-ray absorption coefficient ($\mu_{CoSi2}$) of a $CoSi_2$ film with a thickness of 10 nm is obtained by calculation and is 2% at 1300 eV at which the hard X-rays from arsenic are observed. In the same manner, the values of $\mu_{Co2Si}$ and $\mu_{CoSi}$ are also obtained. The x-ray absorption coefficient of a cobalt film with a thickness of 10 nm is 5% from FIG. 6. In this manner, all the absorption coefficients $\mu_{AsY}$ and $I_{Asini}$ are determined, so that the equation between the intensity $I_{As}$ of the observed hard X-rays from oxygen and the thicknesses $t_{Co2Si}$, $t_{CoSi}$ and $t_{CoSi2}$ of the suicides with respective compositions is obtained.

From the intensity of the observed hard X-rays from cobalt, the equation between this intensity and the thicknesses of the three types of cobalt silicides is obtained. Three unknown thicknesses of the suicides with respective compositions are provided to each of the two equations. Accordingly, fluorescence X-rays applied to a large number of such measurement substrates 200 are measured, and a hypothetical equation expressed by the thicknesses of the three types of cobalt silicides is formed based on the measured values. Then, the thicknesses of the three types of cobalt silicides are calculated using the foregoing simultaneous equations. Since the densities of the respective cobalt silicides are known, the proportions of the three types of cobalt silicides are calculated from these thicknesses.

Once the proportions are obtained from the calculation results, the annealing temperature in the first RTA is determined. Specifically, heat history of the first RTA performed on the measurement substrate 200 determines the proportions of the three types of cobalt silicides uniquely, so that the annealing temperature is calculated backward from the proportions. Even if the annealing temperature in the first RTA slightly varies, the proportions of the three cobalt suicides change relatively largely. Accordingly, the annealing temperature can be obtained from the calculation accurately with the method of this embodiment.

In addition, it is necessary to have the reaction proceed to finally obtain $CoSi_2$ with a relatively low resistance with the second RTA. The optimum annealing temperature in the second RTA is determined by the proportions of the three types of cobalt suicides after the first RTA. Therefore, the annealing temperature in the second RTA is calculated from the proportions so that the second RTA is conducted at the obtained temperature. This calculation may be performed by, for example, using a graph of the relationship between the silicide proportions and the annealing temperature in the second RTA obtained through an experiment beforehand.

In this embodiment, both the fluorescence X-rays (hard X-rays) from cobalt and the fluorescence X-rays (hard X-rays) from arsenic are measured, so that the proportions of a plurality of types of silicides having different compositions are obtained easily with high accuracy. In addition, the annealing temperature in the first RTA is calculated from the proportions with high accuracy. Accordingly, it is possible to set the annealing temperature in the second RTA easily such that an optimum silicide with low resistance and high reliability is formed. Otherwise, it is also possible to set the annealing temperature in the first RTA to increase a margin for the annealing temperature in the second RTA with which the optimum silicide is formed. In this manner, the optimum silicide is formed with high yield of devices.

Now, a method for fabricating the measurement substrate 200 of this embodiment will be described.

First, arsenic as an n-type dopant is implanted into the surface of a silicon substrate 201 in an amount of about $3\times10^{15}$ $cm^{-2}$ by a publicly-known ion implantation technique, thereby forming a doped layer 202. Then, cobalt is deposited by, for example, a sputtering process over the doped layer 202, thereby forming a cobalt metal layer. To prevent oxidation of this cobalt metal layer, titanium nitride is further deposited over the cobalt metal layer, thereby forming a titanium nitride layer.

Thereafter, the measurement substrate 200 in which the layers described above have been formed over the silicon substrate 201 is subjected to heat treatment at a given temperature (a first temperature) of 500° C. for 30 seconds, thus performing a first RTA. The first RTA makes part of the doped layer 202 react with part of the cobalt metal layer, thereby forming a cobalt silicide layer 203. Then, the unreacted cobalt metal layer and the titanium nitride layer are removed with a chemical solution. The cobalt silicide at this time is in a mixed-crystal state, i.e., is made of $Co_2Si$, $CoSi$ and $CoSi_2$. The process up to this state will be referred to as step S101 of preparing the measurement substrate 200.

Next, the measurement substrate 200 after the first RTA, i.e., the doped layer 202 and the cobalt silicide layer 203 over the measurement substrate 201, is irradiated with first X-rays for use in an x-ray fluorescence analysis (step S201). Subsequently, the intensity of hard X-rays emitted from a cobalt element in the cobalt silicide layer 203 and the intensity of hard X-rays emitted from arsenic as the dopant in the doped layer 202 out of the fluorescence X-rays emitted from the layers to a space over the cobalt silicide layer 203 are measured (step S301).

Thereafter, the proportions of the three types of cobalt silicides are calculated from the intensities of the two types of the hard X-rays in the manner described above (step S401), and an annealing temperature in the first RTA is calculated from the proportions (step S501).

Then, a temperature (second temperature) at which a second RTA should be performed is calculated from the proportions, and the second RTA is performed at the obtained temperature so that the reaction proceeds to change substantially all the cobalt silicides into $CoSi_2$ with low resistance. In this manner, the measurement substrate 200 of this embodiment is achieved.

Figure 7:
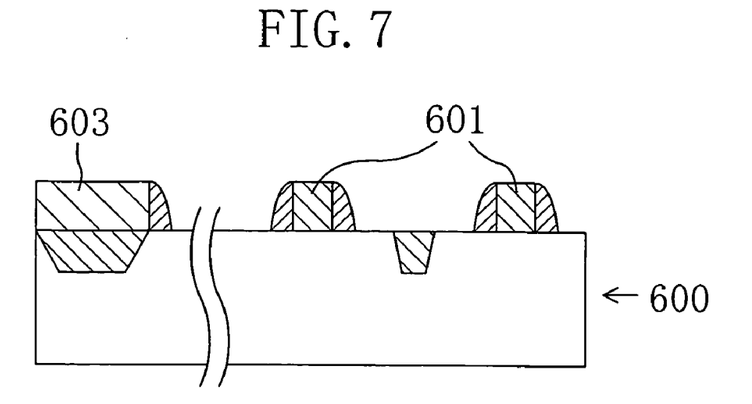
FIG. 7 is a cross-sectional view schematically showing a semiconductor device according to a modified example 2-1.

In this embodiment, the doped layer 202 is not patterned specifically. On the other hand, in a semiconductor device 600 according to a modified example 2-1 of this embodiment, a semiconductor integrated circuit (e.g., a gate electrode 601) is formed by patterning as shown in FIG. 7 and an x-ray photo receiver 603 is provided. In this modified example, an x-ray fluorescence measurement is performed utilizing the x-ray photo receiver 603 to measure the proportions of cobalt silicides and annealing temperatures.

First X-rays for the x-ray fluorescence analysis are applied onto the upper surface of the x-ray photo receiver 603 as an x-ray receiving surface shown in FIG. 7. The area of the x-ray receiving surface is larger than an irradiation spot at a source of the applied X-rays for the x-ray fluorescence analysis. Accordingly, all the first X-rays are applied onto the x-ray photo receiver 603, and all the applied fluorescence X-rays are derived from materials in the x-ray photo receiver 603. Specifically, the applied fluorescence X-rays include only a signal for measuring the proportions of the cobalt silicides and no noise is mixed therein. The area of the x-ray receiving surface is preferably smaller than a 1-mm-square and is more preferably smaller than 500-μm-square.

The x-ray photo receiver 603 is usually formed on, for example, an end of a silicon wafer which is finally disposed of, such as a scribe line, in mass production of transistors. Accordingly, the yield of transistors does not decrease and no additional processes are needed.

The x-ray photo receiver 603 of the modified example 2-1 is fabricated with the same process as the above-described method for fabricating the substrate 200. Specifically, in the process for fabricating the semiconductor device 600, arsenic is implanted into the surface of the substrate including a silicon layer at least at its uppermost portion, thereby forming a doped layer. Subsequently, a cobalt metal layer and a titanium nitride layer are formed over the doped layer, and then a first RTA (annealing) is performed. The x-ray receiving photo receiver 603 thus fabricated is irradiated with X-rays, and the silicide proportions are measured with an x-ray fluorescence analysis. Then, a second RTA (annealing) is performed. Each of the formation process steps and annealing process steps described above is performed concurrently with the corresponding process step for fabricating transistors on the silicon wafer.

In the modified example 2-1, a sidewall or a separation oxide film may be provided around the x-ray photo receiver 603. In a case where such an x-ray photo receiver 603 is provided on the silicon wafer, if an x-ray fluorescence analysis instrument is incorporated in fabrication apparatus beforehand, the proportions of a plurality of types of silicides formed in the semiconductor device during fabrication can be directly measured in an in-line measurement, so that process steps are managed more easily.

Now, modified example 2-2 of this embodiment will be described. The modified example 2-2 is a semiconductor device in which ultra-soft X-rays emitted from arsenic are used for an x-ray fluorescence analysis, instead of hard X-rays from arsenic, and an x-ray photo receiver is provided. Since arsenic has atomic weight much heavier than oxygen and nitrogen, it is possible to use ultra-soft X-rays for an x-ray fluorescence analysis, as well as hard X-rays.

In the modified examples of this embodiment, both the fluorescence X-rays (hard X-rays) emitted from cobalt and the fluorescence X-rays (hard X-rays or ultra-soft X-rays) emitted from arsenic are measured, so that the proportions of a plurality of types of silicides having different compositions are obtained easily in an in-line measurement with high accuracy. The annealing temperature in the first RTA is calculated from the proportions with high accuracy. Accordingly, it is possible to set the annealing temperature in the second RTA such that an optimum silicide with low resistance and high reliability is formed. Otherwise, it is also possible to set the annealing temperature in the first RTA to increase a margin for the annealing temperature in the second RTA with which the optimum silicide is formed. In this manner, an optimum silicide is formed with high yield of devices. If an x-ray fluorescence analysis instrument is incorporated during fabrication such that measurement and calculation are automatically performed under computer control, for example, processes are managed much easily, thus reducing fabrication costs.

Embodiment 3

Figure 8:
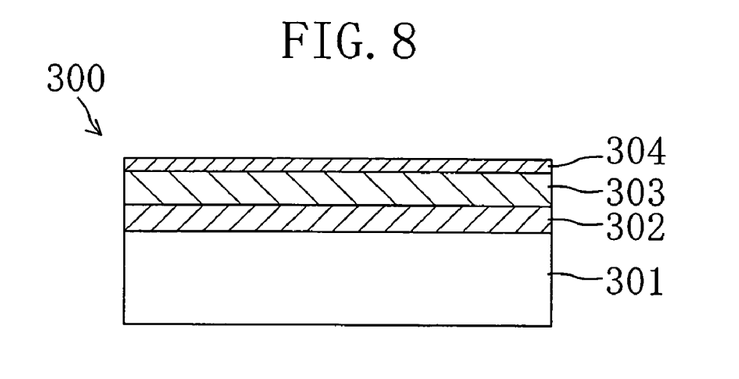
FIG. 8 is a cross-sectional view schematically showing a measurement substrate according to a third embodiment of the present invention.

As shown in FIG. 8, a measurement substrate 300 according to this embodiment includes: a silicon substrate (substrate) 301; a silicon oxide film 302; a doped layer 303 formed by implanting arsenic; and a cobalt silicide layer 304. The silicon oxide film 302, the doped layer 303 and the cobalt silicide layer 304 are formed over the silicon substrate 301 in this order. A plurality of types of cobalt suicides having different compositions included in the cobalt silicide layer 304 are formed by a first RTA and have their proportions changed by a second RTA.

In this embodiment, an x-ray fluorescence analysis is conducted to measure the proportions of the cobalt silicides in the cobalt silicide layer 304. As shown in FIG. 2, this measurement includes: step S101 of preparing the measurement substrate 300; step S201 of irradiating the measurement substrate 300 with first X-rays; step S301 of measuring the intensity of fluorescence X-rays applied; and step S401 of calculating the proportions of the silicides from the intensity of the fluorescence X-rays. A method for measuring the temperature in the first RTA includes step S501 of calculating the annealing temperature from the proportions of the suicides, in addition to the four steps S101, S201, S301 and S401.

The x-ray fluorescence analysis uses hard X-rays emitted from oxygen in the silicon oxide film 302, hard X-rays emitted from arsenic in the doped layer 303 and hard X-rays emitted from cobalt in the cobalt silicide layer 304. The measured intensities of the three types of the hard X-rays are expressed by using unknown thicknesses of three types of cobalt silicides, as described in the first and second embodiments. Accordingly, three equations are formed, associated with the respective three unknown thicknesses. The thicknesses, i.e., the proportions, of the three types of cobalt suicides are calculated uniquely. As a method for calculation, a fundamental element (FE) method may be used, for example.

Once the proportions are obtained from the calculation results, the annealing temperature in the first RTA is determined. Specifically, heat history of the first RTA performed on the measurement substrate 300 determines the proportions of the three types of cobalt silicides uniquely, so that the annealing temperature is calculated backward from the proportions. Even if the annealing temperature in the first RTA slightly varies, the proportions of the three cobalt silicides change relatively largely. Accordingly, the annealing temperature can be obtained from the calculation accurately with the method of this embodiment.

In addition, it is necessary to have the reaction proceed to finally obtain $CoSi_2$ with low resistance with the second RTA. The optimum annealing temperature in the second RTA is determined by the proportions of the three types of cobalt silicides after the first RTA. Therefore, the annealing temperature in the second RTA is calculated from the proportions so that the second RTA is conducted at the obtained temperature. This calculation may be performed by, for example, using a graph of the relationship between the silicide proportions and the annealing temperature in the second RTA obtained through an experiment beforehand.

In this embodiment, fluorescence X-rays (hard X-rays) from oxygen, cobalt and arsenic, respectively, are measured, so that the proportions of a plurality of types of suicides having different compositions are obtained easily with high accuracy. In addition, the annealing temperature in the first RTA is calculated from the proportions with high accuracy. Accordingly, it is possible to set the annealing temperature in the second RTA easily such that an optimum silicide with low resistance and high reliability is formed. Otherwise, it is also possible to set the annealing temperature in the first RTA to increase a margin for the annealing temperature in the second RTA with which the optimum silicide is formed. In this manner, the optimum silicide is formed with high yield of devices.

Now, a method for fabricating the measurement substrate 300 of this embodiment will be described.

First, a silicon oxide film 302 is formed by thermal oxidation in the surface of the silicon substrate 301. Then, a polysilicon layer is formed by, for example, a CVD process thereon. Subsequently, arsenic as an n-type dopant is implanted into the surface of the polysilicon layer in an amount of about $3 \times 10^{15}$ $cm^{-2}$ by a publicly-known ion implantation technique, thereby forming a doped layer 303. Then, cobalt is deposited by, for example, a sputtering process over the doped layer 303, thereby forming a cobalt metal layer. To prevent oxidation of this cobalt metal layer, titanium nitride is further deposited over the cobalt metal layer, thereby forming a titanium nitride layer.

Thereafter, the measurement substrate 300 in which the film and layers described above have been formed over the silicon substrate 301 is subjected to heat treatment at a given temperature (a first temperature) of 500° C. for 30 seconds, thus performing a first RTA. The first RTA makes part of the doped layer 303 react with part of the cobalt metal layer, thereby forming a cobalt silicide layer 304. Then, the unreacted cobalt metal layer and the titanium nitride layer are removed with a chemical solution. The cobalt silicide at this time is in a mixed-crystal state, i.e., is made of $Co_2Si$, $CoSi$ and $CoSi_2$. The process up to this state will be referred to as step S101 of preparing the measurement substrate 300.

Next, the measurement substrate 300 after the first RTA, i.e., the silicon oxide film 302, the doped layer 303 and the cobalt silicide layer 304 over the silicon substrate 301, is irradiated with first X-rays for use in an x-ray fluorescence analysis (step S201). Subsequently, the intensity of hard X-rays emitted from oxygen in the silicon oxide layer 302, the intensity of hard X-rays emitted from a cobalt element in the cobalt silicide layer 304 and the intensity of hard X-rays emitted from arsenic as the dopant in the doped layer 303 out of the fluorescence X-rays emitted from these film and layers to a space over the cobalt silicide layer 304 are measured (step S301).

Thereafter, the proportions of the three types of cobalt silicides are calculated from the intensities of the three types of the hard X-rays (step S401), and an annealing temperature in the first RTA is calculated from the proportions (step S501).

Then, a temperature (second temperature) at which a second RTA should be performed is calculated from the proportions, and the second RTA is performed at the obtained temperature so that the reaction proceeds to change substantially all the cobalt silicides into $CoSi_2$ with low resistance. In this manner, the measurement substrate 300 of this embodiment is achieved.

Figure 9:
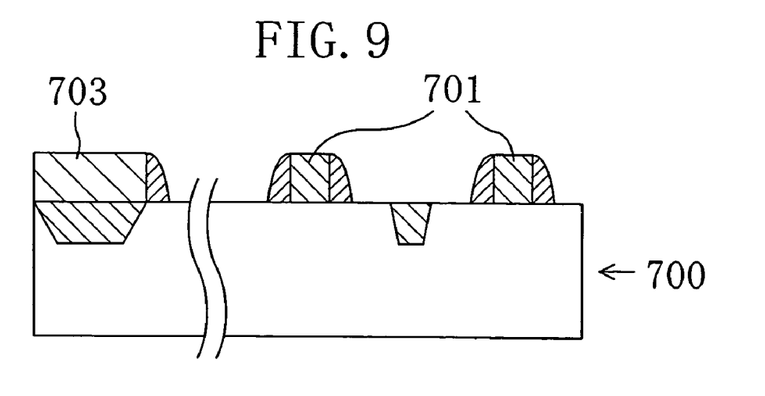
FIG. 9 is a cross-sectional view schematically showing a semiconductor device according to a modified example 3-1.

In this embodiment, the doped layer 303 is not patterned specifically. On the other hand, in a semiconductor device 700 according to a modified example 3-1 of this embodiment, a semiconductor integrated circuit (e.g., a gate electrode 701) is formed by patterning as shown in FIG. 9 and an x-ray photo receiver 703 is provided. In this modified example, an x-ray fluorescence measurement is performed utilizing the x-ray photo receiver 703 to measure the proportions of cobalt silicides and annealing temperatures.

First X-rays for the x-ray fluorescence analysis are applied onto the upper surface of the x-ray photo receiver 703 as an x-ray receiving surface shown in FIG. 9. The area of the x-ray receiving surface is larger than an irradiation spot at a source of the applied X-rays for the x-ray fluorescence analysis. Accordingly, all the first X-rays are applied onto the x-ray photo receiver 703, and all the applied fluorescence X-rays are derived from materials in the x-ray photo receiver 703. Specifically, the applied fluorescence X-rays include only a signal for measuring the proportions of the cobalt suicides and no noise is mixed therein. The area of the x-ray receiving surface is preferably smaller than a 1-mm-square and is more preferably smaller than 500-µm-square.

The x-ray photo receiver 703 is usually formed on, for example, an end of a silicon wafer which is finally disposed of, such as a scribe line, in a process of mass production of transistors. Accordingly, the yield of transistors does not decrease and no additional processes are needed.

The x-ray photo receiver 703 of the modified example 3-1 is fabricated with the same process as the above-described method for fabricating the substrate 300. Specifically, in the process for fabricating the semiconductor device 700, a silicon oxide film is formed in the surface of a substrate including a silicon layer at least at its surface, and a polysilicon layer is formed on the silicon oxide film. Then, arsenic is implanted into the polysilicon layer to form a doped layer, and a cobalt metal layer and a titanium nitride layer are formed over the doped layer. Thereafter, a first RTA (annealing) is performed. The x-ray receiving photo receiver 703 thus fabricated is irradiated with X-rays, and the silicide proportions are measured with an x-ray fluorescence analysis. Then, a second RTA (annealing) is performed. Each of the formation process steps and annealing process steps described above is performed concurrently with the corresponding process step for fabricating transistors on the silicon wafer.

In this modified example 3-1, a sidewall or a separation oxide film may be provided around the x-ray photo receiver 703. In a case where such an x-ray photo receiver 703 is provided on the silicon wafer, if an x-ray fluorescence analysis instrument is incorporated in fabrication apparatus beforehand, the proportions of a plurality of types of suicides formed in the semiconductor device during fabrication can be directly measured in an in-line measurement, so that process steps are managed more easily.

Now, modified examples 3-2, 3-3 and 3-4 of this embodiment will be described. The modified example 3-2 is a semiconductor device in which amorphous silicon is used instead of polysilicon and an x-ray photo receiver is provided. The modified example 3-3 is a semiconductor device in which a silicon nitride film is used instead of the silicon oxide film 302 and an x-ray photo receiver is provided. Measurement of fluorescence X-rays and calculation to obtain the proportions of silicides and annealing temperatures are performed in the same manner as described above. With respect to the fabrication process, the process step of forming a polysilicon layer is substituted by a publicly-known process step of forming an amorphous silicon layer in the modified example 3-2, and the process step of forming a silicon oxide film is substituted by a publicly-known process step of forming a silicon nitride film in the modified example 3-3. Other process steps are the same as those described above. In the modified example 3-3, hard X-rays emitted from nitrogen are used for measurement, instead of hard X-rays emitted from oxygen.

Further, in the modified example 3-4, ultra-soft X-rays from arsenic are used for the x-ray fluorescence analysis, instead of the hard X-rays from arsenic in the modified example 3-1. Since arsenic has atomic weight much heavier than oxygen and nitrogen, it is possible to use ultra-soft X-rays for an x-ray fluorescence analysis, as well as hard X-rays.

In the modified examples of this embodiment, fluorescence X-rays (hard X-rays and ultra-soft X-rays) emitted from oxygen or nitrogen, cobalt and arsenic are measured, so that the proportions of a plurality of types of silicides having different compositions are obtained easily in an in-line measurement with high accuracy. The annealing temperature in the first RTA is calculated from the proportions with high accuracy. Accordingly, it is possible to set the annealing temperature in the second RTA such that an optimum silicide with low resistance and high reliability is formed. Otherwise, it is also possible to set the annealing temperature in the first RTA to increase a margin for the annealing temperature in the second RTA with which the optimum silicide is formed. In this manner, an optimum silicide is formed with high yield of devices. If an x-ray fluorescence analysis instrument is incorporated during fabrication such that measurement and calculation are automatically performed under computer control, for example, processes are managed much easily, thus reducing fabrication costs.

The foregoing embodiments and modified examples are preferred examples, and the present invention is not limited to these examples. The metal species constituting a silicide may be nickel, platinum or tungsten, for example, as well as titanium and silicon, or may be two or more types of metal elements. The dopant may be boron, phosphorus, germanium, antimony or indium, as well as arsenic, or these materials may be used as at the same time.

In the foregoing embodiments and modified examples, either one of the silicon oxide film and the silicon nitride film is formed. Alternatively, both the silicon oxide film and the silicon nitride film may be provided, or a silicon oxynitride film may be provided. In such a case, either hard X-rays from oxygen or hard X-rays from nitrogen may be used or both of these two types of the hard X-rays may be used. The silicon oxide film may contain fluorine and/or nitrogen. It is sufficient that the substrate includes a silicon layer at least at its surface, which is the uppermost portion. The substrate may be an SOI substrate in which a silicon layer is formed on, for example, an insulating substrate or an insulating film. In the case of the SOI substrate, it is necessary to subtract the intensity of hard X-rays emitted from oxygen in the insulating substrate or the insulating film in calculation. In the case of a silicon wafer, it is also sufficient that a silicon layer is provided at least at the surface of the silicon wafer, and the entire silicon wafer is not necessarily made of silicon.

In the foregoing embodiments and modified examples, e.g., in the first embodiment, the substrate 101, the silicon oxide film 102, the polysilicon layer 103 and the titanium silicide layer 104 are formed in this order. However, another layer which does not affect these layers may be provided between the layers.

In addition, methods for forming the silicon oxide film, the silicon nitride film, the polysilicon layer, the amorphous silicon layer and the metal layer are not limited to the methods described above, and various publicly known methods may be used.

The present invention is implemented in the form of the foregoing embodiments and has the following effects.

Since both the hard X-rays from metal constituting silicides and the hard X-rays from oxygen or nitrogen are used, the proportions of a plurality of types of silicides with different compositions are measured easily with high accuracy. In addition, the annealing temperature in the first RTA is easily calculated from the proportions accurately, so that a semiconductor device including a silicide with low resistance and high migration resistance is easily fabricated.

Since both the hard X-rays from metal constituting silicides and the hard X-rays or ultra-soft X-rays from the dopant are used, the proportions of a plurality of types of silicides with different compositions are easily measured with high accuracy. In addition, the annealing temperature in the first RTA is easily calculated from the proportions with high accuracy, so that a semiconductor device including a silicide with low resistance and high migration resistance is easily fabricated.

Since the hard X-rays and/or the ultra-soft X-rays from three elements, i.e., metal constituting suicides, oxygen or nitrogen, and a dopant, are used, the proportions of a plurality of types of suicides with different compositions are measured easily with high accuracy. In addition, the annealing temperature in the first RTA is easily calculated from the proportions accurately, so that a semiconductor device including a silicide with low resistance and high migration resistance is easily fabricated.

What is claimed is:

1. A method for measuring suicide proportions, the method comprising the steps of:
    preparing a measurement substrate including:
        a substrate including a silicon layer at least at the surface thereof;
        a doped layer formed by implanting a dopant into the surface of the silicon layer; and
        a silicide layer formed in the surface of the doped layer by annealing at a given temperature and made of a plurality of types of silicides having different combining ratios of metal and silicon;
    irradiating the measurement substrate with X-rays;
    measuring the intensity of hard X-rays or ultra-soft X-rays emitted from the dopant in the doped layer by the irradiation with the X-rays, and the intensity of hard X-rays emitted from the metal in the silicide layer by the irradiation with the X-rays;

calculating proportions of the plurality of types of silicides in the silicide layer, from either the intensities of the two types of the hard X-rays or the intensities of the ultra-soft X-rays and the hard X-rays emitted from the metal; and calculating the given temperature from either the intensities of the two types of the hard X-rays or the intensities of the ultra-soft X-rays and the hard X-rays emitted from the metal.

2. The method of claim 1, wherein the metal contains a metal element having a high melting point.

3. The method of claim 1, wherein the metal is made of at least one element selected from the group consisting of titanium, cobalt, nickel and platinum.

4. The method of claim 1, wherein the dopant is made of at least one material selected from the group consisting of boron, phosphorus, arsenic, germanium, antimony and indium.

5. A method for measuring an annealing temperature, the method comprising the steps of:

preparing a measurement substrate including:
a substrate including a silicon layer at least at the surface thereof;
a doped layer formed by implanting a dopant into the surface of the silicon layer; and
a metal layer formed over the doped layer;

annealing the measurement substrate at a given temperature, thereby changing at least part of the doped layer and at least part of the metal layer into a silicide layer made of a plurality of types of silicides having different combining ratios of metal and silicon;

irradiating the measurement substrate with X-rays after the step of forming the suicide layer has been performed;

measuring the intensity of hard X-rays or ultra-soft X-rays emitted from the dopant in the doped layer by the irradiation with the X-rays, and the intensity of hard X-rays emitted from the metal in the silicide layer by the irradiation with the X-rays; and calculating the given temperature from either the intensities of the two types of the hard X-rays or the intensities of the ultra-soft X-rays and the hard X-rays emitted from the metal.

6. The method of claim 5, wherein the metal contains a metal element having a high melting point.

7. The method of claim 5, wherein the metal is made of at least one element selected from the group consisting of titanium, cobalt, nickel and platinum.

8. The method of claim 5, wherein the dopant is made of at least one material selected from the group consisting of boron, phosphorus, arsenic, germanium, antimony and indium.

* * * * *